United States Patent [19]

Nordby et al.

[11] E Re. 29,319

[45] Reissued July 26, 1977

[54] DRAINAGE SYSTEM FOR INCISIONS OR WOUNDS IN THE BODY OF AN ANIMAL

[75] Inventors: Harvey M. Nordby, Buffalo Grove; John L. Nolan, Glenview; Bremen I. Johnson, Cary, all of Ill.

[73] Assignee: Hollister Incorporated, Chicago, Ill.

[21] Appl. No.: 737,142

[22] Filed: Oct. 29, 1976

Related U.S. Patent Documents

Reissue of:

[64] Patent No.: 3,954,105
Issued: May 4, 1976
Appl. No.: 565,614
Filed: Apr. 7, 1975

U.S. Applications:

[63] Continuation of Ser. No. 402,047, Oct. 1, 1973, abandoned.

[51] Int. Cl.[2] ..... A61F 5/44

[52] U.S. Cl. ..... 128/275; 128/283; 128/154

[58] Field of Search ..... 128/275, 283, 294, 295, 128/132, 154, 155, 156

[56] References Cited

U.S. PATENT DOCUMENTS

| | | | |
|---|---|---|---|
| 2,367,690 | 1/1945 | Purdy | 128/132 |
| 3,026,874 | 3/1962 | Stevens | 128/154 |

*Primary Examiner*—Robert W. Michell
*Assistant Examiner*—Henry S. Layton
*Attorney, Agent, or Firm*—Tilton, Fallon, Lungmus, Chestnut & Hill

[57] ABSTRACT

The invention provides a combination of a sheet of thin pliable material adapted to be placed in sealing engagement with the skin of a patient in the location of a body opening made by an incision or wound, with the sheet being adapted to have an aperture formed therein to expose the opening, together with a removable cap preferably of transparent plastic material which can be adhesively secured to the outer face of the sheet. Drains placed in the body opening can be observed through the cap and the opening can be treated and the tubes withdrawn in increments by simply removing the cap which thereafter can be replaced.

5 Claims, 8 Drawing Figures

10
11
12
13
14
15

11
10
14
16
17
18
18

10
14
16
17
18
18

20
21
22
23
24
25
26
28

DRAINAGE SYSTEM FOR INCISIONS OR WOUNDS IN THE BODY OF AN ANIMAL

Matter enclosed in heavy brackets [ ] appears in the original patent but forms no part of this reissue specification; matter printed in italics indicates the additions made by reissue.

CROSS-REFERENCE

This application is a continuation of our copending application Ser. No. 402,047, filed Oct. 1, 1973, and assigned to the same assignee as the instant application, and now abandoned.

BACKGROUND OF THE INVENTION

Many instances arise which require the treatment of an incision or wound in the body of an animal, particularly a human. In many cases, drain tubes are inserted into the body through an incision or at the site of an incision or wound and drainage of fluid from the interior body takes place. Usually the drains are tubular, of soft, pliable, plastic material and the drainage itself occurs primarily along the exterior surface of the tube. As healing progresses, the tubes are withdrawn in increments on a more or less regular (for example, daily) basis, and are withdrawn completely as healing nears completion. It is necessary for the physician treating the patient to have access to the wound or incision area to observe the progress of healing and detect infections which may arise, as well as to have access to the tubes so that they may be incrementally withdrawn during the course of treatment. Inasmuch as it is undesirable to permit the incision or wound to be exposed for any long periods of time because of the possibility of infection from the surrounding bedclothing or the air itself, it has heretofore been the practice to suitably bandage the patient thereby covering the site of the incision. Obviously, it was necessary for the physician to remove the bandage in order to inspect the incision or wound, to withdraw the tubular drains, and otherwise to treat the patient. This practice not only required repeated bandaging of the patient, but was unsatisfactory inasmuch as the bandages themselves became saturated with fluid draining from the body, and otherwise presented difficulties to the physician and varying degrees of discomfort to the patient.

BRIEF SUMMARY OF THE INVENTION

According to the present invention, there is provided a thin, pliable sheet of plastic material which may be adhesively secured to the skin of the patient surrounding the opening (wound or incision) in the body of the patient. If desired, that portion of the sheet closest to and surrounding the opening may be provided with a blanket of gelatinous material containing gum karaya. The sheet, and if a blanket is provided also the blanket, are adapted to be provided with an aperture to expose the opening and the skin immediately adjacent thereto, as well as to expose any tube or tubes which may have been positioned in the opening by the physician in order to promote drainage of fluids from the interior of the body. A cap of transparent plastic material is removably secured to the opposite face of the sheet and may be located thereon so as to surround and hence isolate the body opening. In the event drainage from the opening is relatively heavy, a plastic bag may be interposed between the outer surface of the sheet and the cap so that fluid draining from the opening may freely enter the bag and hence be carried away from the wound or incision area. The outer wall of the bag is provided with an opening adapted to be covered by the removable cap so that again inspection of and access to the wound or incision area is readily attainable.

DETAILED DESCRIPTION OF THE PREFERRED EMBODIMENT

Figure 1:
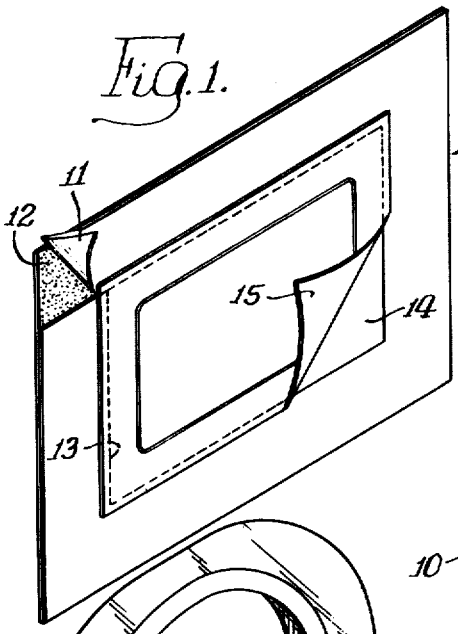
FIG. 1 is an elevational view of the sheet of plastic material forming a part of the drainage system of the present invention.
Figure 2:
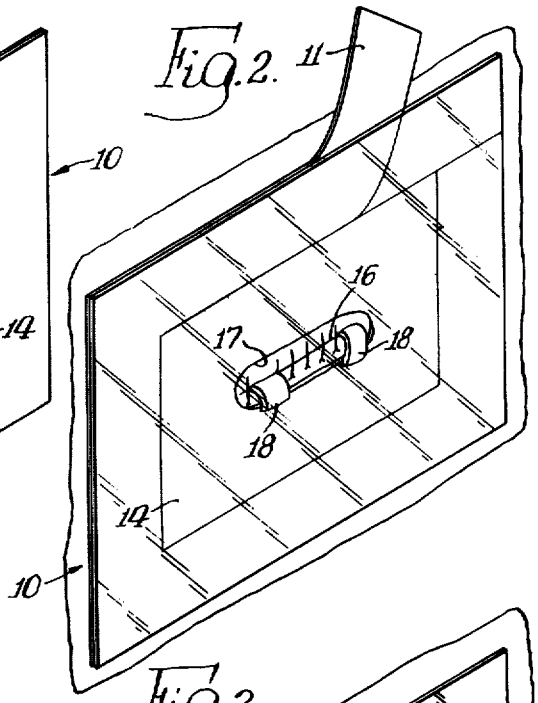
FIG. 2 is a view like FIG. 1 of the opposite face of said sheet.
Figure 3:
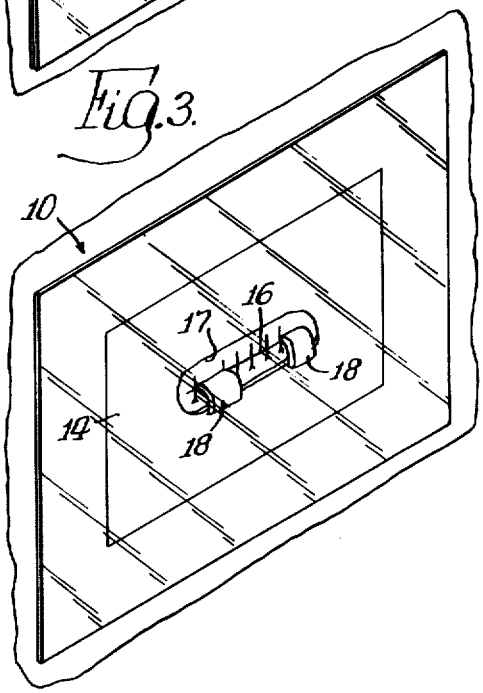
FIG. 3 is a view like FIG. 2 showing an aperture formed therein.
Figure 4:
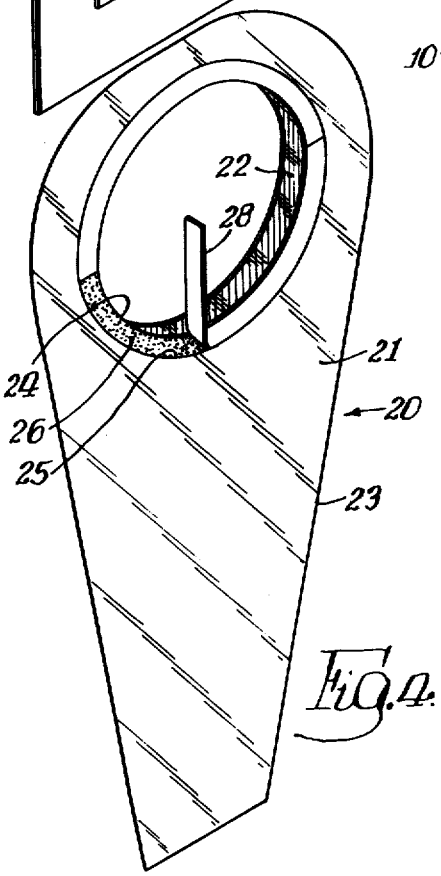
FIG. 4 is an elevational view of a bag structure to be used in the combination of the present invention.

Referring now to the drawings, there is shown a generally rectangular sheet 10 of plastic material covered along its edges by a peel-off strip 11 of paper or similar material to expose an adhesive-carrying portion 12. The central portion of the sheet 10 carries a generally rectangular blanket 14 of gelatinous material. Preferably, the gelatinous material includes karaya gum and may be made, for example, of a formulation similar to the karaya sealing ring disclosed in U.S. Pat. No. 3,302,647. The blanket 14 is covered with a peel-off sheet 15 which, together with the strip 11, may be removed when the sheet is to be positioned over a wound or incision (hereinafter called opening) in the body of a patient. Such an opening is indicated at 16 in FIG. 2. Before placing the sheet and the blanket carried thereby over the opening 16, a suitable aperture such as the aperture 17 is formed in each so as to expose the opening 16 therethrough. The sheet 10 and in the event it carries a blanket, the blanket 14, are pressed into sealing engagement with the skin of the patient so as to isolate the opening in the body from the surrounding tissue and, of course, expose the tubular drain 18 which extends therefrom.

In many instances there is a substantial quantity of fluid draining from the opening 16 primarily along the exterior surface of the tube or tubes 18, and hence the present invention may provide means for collecting and segregating such fluids so as to avoid discomfort for the patient and to prevent irritation or infection which might otherwise occur. To this end there is provided a bag 20 of flexible plastic material. The bag 20 is provided with an inner wall 21 and an outer wall 22, with the walls being sealed together along their peripheral edges 23 to form a bag. The inner wall 21 is provided with a relatively large hole 24 therein while the outer wall 22 is similarly provided with a hole 25 placed immediately opposite the hole 24. Surrounding each of the holes and secured to the faces of the walls forming the bag are circular rings 26 and 27. The rings are formed of relatively stiff but deformable plastic material, and the face of the ring 26 on the inner wall is provided with an adhesive covered by a peel strip 28. Means in the form of separators are provided between the two rings to insure that the walls 21 and 22 remain separated in the area surrounding the holes so that fluid may drain into the bag without obstruction.

Means in the form of a removable cover or cap are provided for covering the hole 25 in the outer wall 22. The cap *33 of thin plastic material* may take the form shown in FIG. 6, which includes a *relatively stiff but deformable* ring 30 of plastic material *of approximately the same diameter as ring 27 in outer wall 22 and* having an adhesive-carrying face 31 covered by a peel strip 32. Secured to the opposite face of the ring 30 is a cap 33 of transparent plastic material.

In using the drainage system of the present invention the peel strip 15 may be removed from the central portion of the sheet 10 and a suitable aperture formed in the blanket 14 and the underlying portion of the sheet 10 of a size sufficient to accommodate and expose the opening 16 in the body of the patient. Peel strips 11 are then removed and the [adhesivebearing] *adhesive-bearing* face of the sheet 10 and the blanket 14 are pressed against the skin of the patient for adherence thereto. As the aperture 17 closely approximates the size and shape of the opening 16, it can readily be seen that the tissue area surrounding the opening is isolated therefrom. This isolation performs a twofold function. First, it protects the surrounding skin area from irritation by the fluids draining from the body, and simultaneously helps to prevent the opening in the body from being contaminated by bacteria or other sources of infection which may be located on the adjoining skin.

Figure 8:
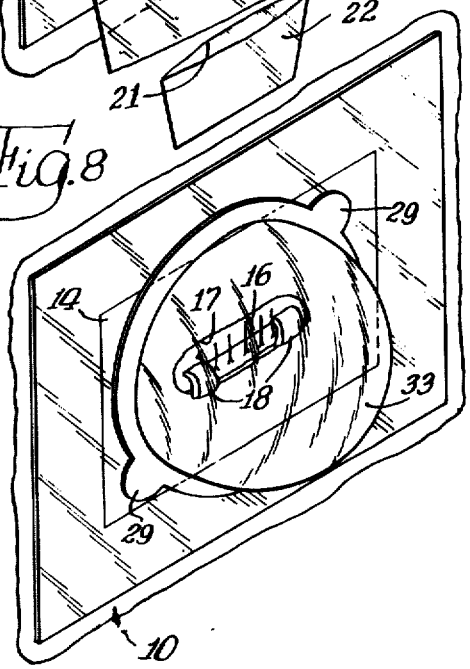
FIG. 8 is a somewhat modified form of the invention wherein the cap of FIG. 6 is sealingly engaged directly to the sheet of FIG. 3 without the interposition of a bag.
Figure 6:
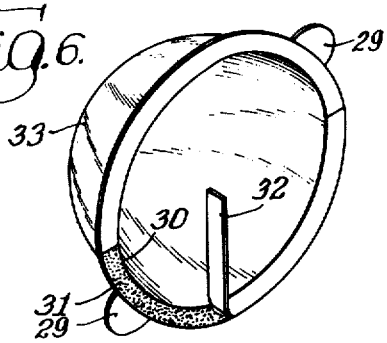
FIG. 6 is an elevational view of a cap to be used in the combination of the invention.

If the drainage is relatively light, the cap of FIG. 6 may be pressed directly on the outer face of the sheet 10 as shown in FIG. 8. To this end the peel strip 32 is removed from the ring 30 and the adhesive face 31 pressed against the outer face of the sheet 10 as shown in FIG. 8.

Figure 5:
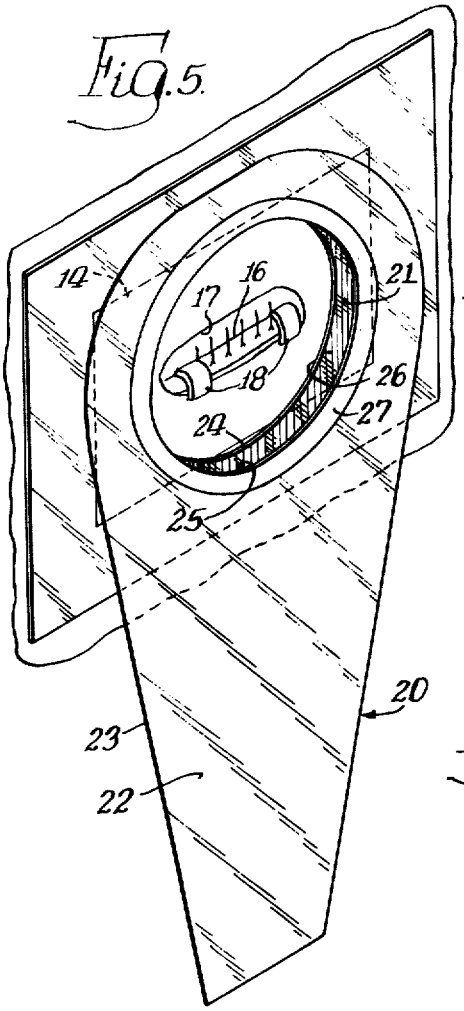
FIG. 5 is an elevational view showing the bag of FIG. 4 adhesively secured to the sheet of FIG. 3.
Figure 7:
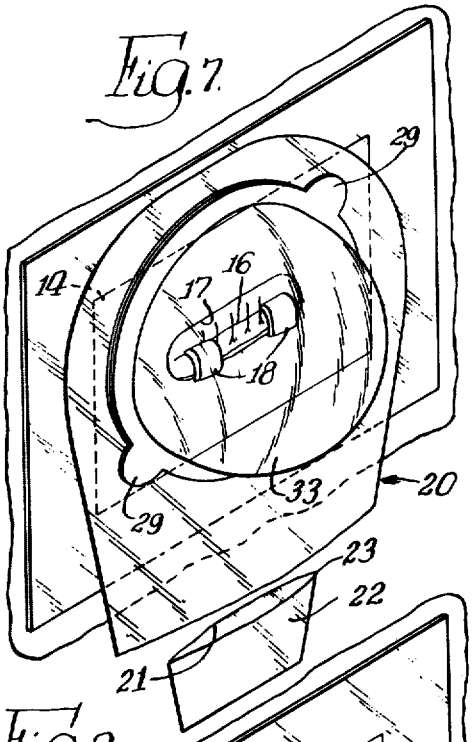
FIG. 7 is a view like FIG. 5, partially broken away, and with the cap of FIG. 6 positioned thereon.

If however, substantial drainage is expected, the cap of FIG. 6 is used in conjunction with the bag 20. To this end the peel strip 28 is removed and the adhesive-carrying face 26 pressed against the outer face of the sheet 10 as shown in FIG. 5. The peel strip 32 is then removed from the cap and the adhesive-bearing ring is pressed against the ring 27 as shown in FIG. 7.

It is clear that the physician or surgeon in charge of the case can visually inspect the opening and the drainage through the transparent cap 33. Treatment of the opening area and partial removal of the tubes may be effected merely by removing the cap 33, treating the patient, and then returning the cap to its original position. To facilitate removal of the cap, pull-tabs 29 are provided which may be grasped by the fingers of the physician or surgeon to remove the cap. The ends of the tubular drains 18 may be led directly into the space maintained between the inner and outer walls of the bag so as to facilitate drainage from the opening directly into the bag.

Thus it will be seen that the care of the patient will be facilitated, the discomfort of repeated bandage changing will be avoided, and frequent inspection of the wound area is permitted by employment of the drainage system of the present invention.

We claim:

1. A drainage system for draining fluids from an opening such as a wound or incision in the body of an animal, said system being usable in combination with a drain having a portion within the body and a portion extending outwardly of the body through said opening, said drainage system comprising a sheet of gelatinous material having a size sufficient to cover the wound, the drain and a substantial portion of the external area of the body surrounding the opening, said sheet having a face adapted to be placed in direct contact with and thereby to sealingly engage the external area of the body surrounding the opening, said sheet being adapted to have an aperture formed therein exposing only said opening and the drain therein while covering and isolating the area of the body surrounding said opening and drain, ring forming means of relatively stiff but deformable plastic material, means for securing one side of the ring forming means in sealing engagement with the opposite face of said sheet surrounding said aperture, and a cap of thin transparent plastic material having an edge portion sealingly engaging the opposite side of said ring forming means, said cap being removable to give access to said opening and said drain.

2. A drainage system for draining fluids from an opening such as a wound or incision in the body of an animal, said system being usable in combination with a drain having a portion within the body and a portion extending outwardly of the body through said opening, said drainage system comprising a sheet of soft, pliable, plastic material, a blanket of gelatinous material adhered to one face of the sheet to be placed in contact with and thereby to sealingly engage the external area of the body surrounding the opening, said sheet and blanket being adapted to have an aperture formed therein exposing only said opening and the drain therein while covering and isolating the area of the body surrounding said opening and drain, ring forming means of relatively stiff but deformable plastic material, means for securing one side of the ring forming means in sealing engagement with the opposite face of said sheet surrounding said aperture, and a cap of thin transparent plastic material having an edge portion sealingly engaging the opposite side of said ring forming means, said cap eing removable to give access to said opening and said drain.

3. A drainage system for draining fluids from an opening such as a wound or incision in the body of an animal, said system being usable in combination with a drain having a portion within the body and a portion extending outwardly of the body through said opening, said drainage system comprising a sheet of soft, pliable material having a face to be placed in contact with and thereby to sealingly engage the external area of the body surrounding the opening, said sheet being adapted to have an aperture formed therein exposing only said opening and the drain therein while covering and isolating the area of the body surrounding said opening and drain, a bag of thin plastic material having an inner wall and an outer wall, said walls being secured together at their peripheral edges to form a bag and said walls having opposed holes therein, means for securing the inner wall of the bag to the opposite face of said sheet with the hole in the inner wall surrounding said aperture, a cap of thin plastic material, and means for securing the cap to the outer wall of the bag in position to surround the hole therein, said cap being transparent to permit visual inspection of said opening and drain and said cap being removable to give access to said opening and said drain.

4. A drainage system for draining fluids from an opening such as a wound or incision in the body of an animal, said system being usable in combination with a drain having a portion within the body and a portion extending outwardly of the body through said opening, said drainage system comprising a sheet of soft, pliable, plastic material, a blanket of gelatinous material adhered to one face of the sheet to be placed in contact with and thereby to sealingly engage the external area of the body surrounding the opening, said sheet and blanket being adapted to have an aperture formed therein exposing only said opening and the drain therein while covering and isolating the area of the body surrounding said opening and drain, a bag of thin plastic material having an inner wall and an outer wall, said walls being secured together at their peripheral edges to form a bag and said walls having opposed holes therein, a relatively stiff but deformable ring surrounding each of said holes and sealed to said walls, an adhesive-carrying face on the ring surrounding the hole in the inner wall for securing the bag to the opposite face of said sheet with the hole in the inner wall surrounding said aperture, a cap of thin plastic material secured to a third relatively stiff but deformable ring of approximately the same diameter as the ring in the outer wall, and means for removably securing said third ring to the ring in the outer wall to permit the cap to be removably secured to the outer wall of the bag.

5. A drainage system for draining fluids from an opening such as a wound or incision in the body of an animal, said system being usable in combination with a drain having a portion within the body and a portion extending outwardly of the body through said opening, said drainage system comprising a solid sheet having no discontinuities therein and being formed of soft gelatinous material, said sheet having a face adapted to be placed in direct contact with and thereby to sealingly engage the external area of the body surrounding the opening, said sheet being adapted to have an aperture formed therein exposing only said opening and the drain therein while covering and isolating the area of the body surrounding said opening and drain, ring forming means of relatively stiff but deformable plastic material, means for securing one side of the ring forming means in sealing engagement with the opposite face of said sheet surrounding said aperture, and a cover member of thin plastic material having an edge portion sealingly engaging the opposite side of said ring forming means, said cover member being removable to give access to said opening and said drain.

* * * * *

UNITED STATES PATENT AND TRADEMARK OFFICE

CERTIFICATE OF CORRECTION

PATENT NO. : RE 29319

DATED : July 26, 1977

INVENTOR(S) : Harvey M. Nordby, John L. Nolan, Bremen I. Johnson

It is certified that error appears in the above-identified patent and that said Letters Patent are hereby corrected as shown below:

Column 4, line 45, change "eing" to --being.

Signed and Sealed this

*Eighth* Day of *November 1977*

[SEAL]

*Attest:*

RUTH C. MASON
*Attesting Officer*

LUTRELLE F. PARKER
*Acting Commissioner of Patents and Trademarks*